United States Patent [19]
Valdes et al.

[11] Patent Number: 5,882,652
[45] Date of Patent: Mar. 16, 1999

[54] EMPTY CANINE PARVOVIRUS CAPSIDS HAVING CPV RECOMBINANT VP2 AND VACCINES HAVING SUCH CAPSIDS

[75] Inventors: Elena Cortes Valdes; Carmen Vela Olmo; Jose Ignacio Casal Alvarez, all of Madrid, Spain

[73] Assignee: Immunologia Y Genetica Aplicada, S.A., Madrid, Spain

[21] Appl. No.: 317,785

[22] Filed: Oct. 4, 1994

Related U.S. Application Data

[63] Continuation of Ser. No. 983,577, filed as PCT/FR92/00031 Mar. 26, 1992 published as WO92/17205 Oct. 15, 1992, abandoned.

[30] Foreign Application Priority Data

Mar. 26, 1991 [ES] Spain ..................... 9100844

[51] Int. Cl.$^6$ .................................. A61K 39/215
[52] U.S. Cl. .................. 424/221.1; 424/199.1; 424/818; 530/418; 530/419
[58] Field of Search .............. 424/221.1, 199.1, 424/818; 530/418, 419

[56] References Cited

U.S. PATENT DOCUMENTS

| | | |
|---|---|---|
| 4,857,634 | 8/1989 | Minor et al. . |
| 4,870,023 | 9/1989 | Fraser et al. . |
| 4,971,793 | 11/1990 | Wood et al. . |
| 5,508,186 | 4/1996 | Young et al. . |

FOREIGN PATENT DOCUMENTS

| | | |
|---|---|---|
| 0341611 | 5/1989 | European Pat. Off. . |
| 8802026 | 3/1988 | WIPO . |

OTHER PUBLICATIONS

Vialerd et al. J. Virol. 64(1):37–50 Jan. 1990.
Tretschin et al. J.Gen.Virol. 61:33–41, 1982.
Reed et al. J. Virol 62(1):226–76, 1988.
Lopez et al. J. Virol 66(5):2748–53, May 1992.
"Antibodies, A Laboratory Manual" Ed. E.Harlow and D. Lane Cold Spring Harbor Laboratory 1988 see pp. 298, 446 & 447.
Kajigaya et al. PNAS (88):4646–4650 Jun. 1991.
Harlow and Lane (Ed.) "Antibodies, A Laboratory Manual", published in 1988 by Cold Spring Harbor Laboratory, see pp. 98, 99, 298, 299, 446, 447, and 450.

*Primary Examiner*—Anthony C. Caputa
*Attorney, Agent, or Firm*—Harrison & Egbert

[57] ABSTRACT

The present invention is a method for the production of a subunit vaccine against canine parvovirus (CPV). The method includes the step wherein a recombinant protein VP2 of CPV is obtained by using the replication of a recombinant baculovirus wherein the gene corresponding to VP2 has been previously inserted in cells of a permissive host. The protein VP2 obtained has the capacity of forming empty VP2 capsids with high immunogenicity and can be provided as a vaccine formulation for protecting dogs against CPV infection the recombinant baculovirus AcMN-PV.pCPVEx17 expresses the VP2 of CPV in conditions making possible the formulation of pseudo-viral capsids.

2 Claims, 7 Drawing Sheets

FIG. 1A

CPVVP2   5' → 3'

```
ATG AGT GAT GGA GCA GTT CAA CCA GAC GGT GGT CAA CCT GCT GCT AGA AAT GAA AGA GCT     60
Met Ser Asp Gly Ala Val Gln Pro Asp Gly Gly Gln Pro Ala Ala Arg Asn Glu Arg Ala

ACA GGA TCT GGG AAC GGG TCT GGA GGC GGT GGT GGG GGT TCT GGG GGT GTG GGT ATT        120
Thr Gly Ser Gly Asn Gly Ser Gly Gly Gly Gly Gly Gly Ser Gly Gly Val Gly Ile

TCT ACG GGT ACT TTC AAT AAT CAG ACG GAA TTT AAA TTT TTG GAA AAC GGA TGG GTG GAA    180
Ser Thr Gly Thr Phe Asn Asn Gln Thr Glu Phe Lys Phe Leu Glu Asn Gly Trp Val Glu

ATC ACA GCA AAC TCA AGC AGA CTT GTA CAT TTA AAT ATG CCA GAA AGT GAA AAG GAT AGA    240
Ile Thr Ala Asn Ser Ser Arg Leu Val His Leu Asn Met Pro Glu Ser Glu Lys Asp Arg

AGA GTG GTT AAT AAT ATG GAT AAA ACT GCA GTT AAC GGA AAC ATG GCT TTA GAT GAT        300
Arg Val Val Asn Asn Met Asp Lys Thr Ala Val Asn Gly Asn Met Ala Leu Asp Asp

ATT CAT GCA CAA ATT GTA ACA CCT TGG TCA TTG GTT GAT GCA AAT GCT TGG GGA GTT TGG    360
Ile His Ala Gln Ile Val Thr Pro Trp Ser Leu Val Asp Ala Asn Ala Trp Gly Val Trp

TTT AAT CCA GGA GAT TGG CAA CTA ATT GTT AAT ACT ATG AGT GAG TTG CAT TTA GTT AGT    420
Phe Asn Pro Gly Asp Trp Gln Leu Ile Val Asn Thr Met Ser Glu Leu His Leu Val Ser
```

FIG. 1B

```
TTT  GAA  CAA  GAA  ATT  AAT  GTT  TTT  AAG  ACT  GTT  TCA  GAA  TCT  GCT  ACT  CAG  CCA
Phe  Glu  Gln  Glu  Ile  Asn  Val  Phe  Lys  Thr  Val  Ser  Glu  Ser  Ala  Thr  Gln  Pro
                                          450                                         480

CCA  ACT  AAA  GTT  TAT  AAT  AAT  GAT  TTA  ACT  GCA  TCA  TTG  ATG  GTT  GCA  TTA  GAT  AAT
Pro  Thr  Lys  Val  Tyr  Asn  Asn  Asp  Leu  Thr  Ala  Ser  Leu  Met  Val  Ala  Leu  Asp  Asn
                                          510                                         540

AAT  ACT  ATG  CCA  TTT  ACT  CCA  GCA  GCT  ATG  AGA  TCT  GAG  ACA  TTG  GGT  TTT  TAT  CCA
Asn  Thr  Met  Pro  Phe  Thr  Pro  Ala  Ala  Met  Arg  Ser  Glu  Thr  Leu  Gly  Phe  Tyr  Pro
                                          570                                         600

AAA  CCA  ACC  ATA  CCA  ACT  CCA  TGG  AGA  TAT  TTT  CAA  TGG  GAT  AGA  ACA  TTA  ATA  CCA
Lys  Pro  Thr  Ile  Pro  Thr  Pro  Trp  Arg  Tyr  Phe  Gln  Trp  Asp  Arg  Thr  Leu  Ile  Pro
                                          630                                         660

TCT  CAT  ACT  GGA  ACT  ATT  GAA  AAT  TCT  ACA  CCA  AAT  ATA  TAC  CAT  GGT  ACA  GAT  GAT
Ser  His  Thr  Gly  Thr  Ile  Glu  Asn  Ser  Thr  Pro  Asn  Ile  Tyr  His  Gly  Thr  Asp  Asp
                                          690                                         720

GTT  CAA  TTT  TAT  ACT  GTG  CCA  GTA  CAC  TTA  AGA  ACA  GAT  CCA  GAT  GAA
Val  Gln  Phe  Tyr  Thr  Val  Pro  Val  His  Leu  Arg  Thr  Asp  Pro  Asp  Glu
                                    750                                    780

TTT  GCT  ACA  GGA  ACA  TTT  TTT  GAT  TGT  AAA  CCA  TGT  AGA  CTA  ACA  CAT  ACA  TGG  CAA
Phe  Ala  Thr  Gly  Thr  Phe  Phe  Asp  Cys  Lys  Pro  Cys  Arg  Leu  Thr  His  Thr  Trp  Gln
                                          810                                         840
```

FIG. 1C

```
ACA AAT AGA GCA TTG GGC TTA CCA CCA TTT CTA AAT TCT TTG CCT CAA TCT GAA GCT GCA
Thr Asn Arg Ala Leu Gly Leu Pro Pro Phe Leu Asn Ser Leu Pro Gln Ser Glu Ala Ala
                                    870                                      900

ACT AAC TTT GGT GAT ATA GGA GTT CAA CCA GAT AAA AGA CGT GGT GTA ACT CAA ATG GGA
Thr Asn Phe Gly Asp Ile Gly Val Gln Pro Asp Lys Arg Arg Gly Val Thr Gln Met Gly
                                    930                                      960

AAT ACA AAC TAT ATT ACT GAA GCT ACT ATG AGA CCA GCT GAG GTT TAT AGT GCA
Asn Thr Asn Tyr Ile Thr Glu Ala Thr Met Arg Pro Ala Glu Val Tyr Ser Ala
                                    990                                     1020

CCA TAT TAT TCT TTT GAG GCG TCT ACA CAA GGG CCA TTT AAA ACA CCT ATT GCA GGA
Pro Tyr Tyr Ser Phe Glu Ala Ser Thr Gln Gly Pro Phe Lys Thr Pro Ile Ala Gly
                                   1050                                     1080

CGG GGA GCG CAA ACA TAT GAA AAT ACC ACC CAA AAT GAT GGT GCA GAT CCA AGA GCA TTT
Arg Gly Ala Gln Thr Tyr Glu Asn Thr Thr Gln Asn Asp Gly Ala Asp Pro Arg Ala Phe
                                   1110                                     1140

GGT AGA CAA CAT GGT CAA AAA ACT CAA ACA ACC ACA GGA GAA ACA CCT GAG AGA TTT ACA
Gly Arg Gln His Gly Gln Lys Thr Gln Thr Thr Thr Gly Glu Thr Pro Glu Arg Phe Thr
                                   1170                                     1200

ATA GCA CAT CAA GAT ACA GGA AGA TAT CCA GAA GGA GAT TGG ATT CAA AAT ATT AAC TTT
Ile Ala His Gln Asp Thr Gly Arg Tyr Pro Glu Gly Asp Trp Ile Gln Asn Ile Asn Phe
                                   1230                                     1260
```

FIG. 1D

```
                                                                              1320
AAC CTT CCT GTA ACG AAT GAT AAT GTA TTG CTA CCA ACA GAT CCA ATT GGA GGT AAA ACA
Asn Leu Pro Val Thr Asn Asp Asn Val Leu Leu Pro Thr Asp Pro Ile Gly Gly Lys Thr
                                                                              1380
GGA ATT AAC TAT ACT AAT ATA TTT ACT TAT GGT CCT TTA ACT GCA TTA ACT AAT GTA
Gly Ile Asn Tyr Thr Asn Ile Phe Thr Tyr Gly Pro Leu Thr Ala Leu Thr Asn Asn Val
                                                                              1440
CCA CCA GTT TAT CCA AAT GGT CAA ATT TGG GAT AAA GAA TTT GAT ACT GAC TTA AAA CCA
Pro Pro Val Tyr Pro Asn Gly Gln Ile Trp Asp Lys Glu Phe Asp Thr Asp Leu Lys Pro
                                                                              1500
AGA CTT CAT GTA AAT GCA CCA TTT CAA AAT TGT GTT CCT GGT CAA TTA TTT GTA
Arg Leu His Val Asn Ala Pro Phe Gln Asn Cys Val Pro Gly Gln Leu Phe Val
                                                                              1560
AAA GTT GCG CCT AAT TTA ACA AAT GAA AAT AAT TGT CCT GAT GCA TCT GCT AAT ATG TCA AGA
Lys Val Ala Pro Asn Leu Thr Asn Glu Asn Asn Cys Pro Asp Ala Ser Ala Asn Met Ser Arg
                                                                              1620
ATT GTA ACT TAC TCA GAT TTT TGG TGG AAA GGT AAA TTA GTA TTT AAA GCT AAA CTA AGA
Ile Val Thr Tyr Ser Asp Phe Trp Trp Lys Gly Lys Leu Val Phe Lys Ala Lys Leu Arg
                                                                              1680
GCC TCC CAT ACT TGG AAT CCA ATT CAA CAA ATG AGT ATT AAT GTA GAT AAC CAA TTT AAC
Ala Ser His Thr Trp Asn Pro Ile Gln Gln Met Ser Ile Asn Val Asp Asn Gln Phe Asn
```

FIG. 1E

```
TAT GTA CCA AGT AAT ATT GGA GGT ATG AAA ATT GTA TAT GAA AAA TCT CAA CTA GCA CCT
Tyr Val Pro Ser Asn Ile Gly Gly Met Lys Ile Val Tyr Glu Lys Ser Gln Leu Ala Pro
                                    1710                                    1740

AGA AAA TTA TAT TA
Arg Lys Leu Tyr
```

EMPTY CANINE PARVOVIRUS CAPSIDS HAVING CPV RECOMBINANT VP2 AND VACCINES HAVING SUCH CAPSIDS

This is a continuation of copending applications Ser. No. 07/983,577 filed on 26 Jan. 1993, International Application PCT/ES92/00031 filed on 26 Mar. 1992 published as WO92/17205 Oct. 15, 1992 and which designated the U.S.

FIELD OF THE INVENTION

The present invention relates in general to viral proteins and to assays and vaccines using the same and, in particular, to a protein related to the major antigen (VP2) of the Canine Parvovirus (CPV) capsid. Such protein was produced in an expression vector of baculoviruses multiplied in a cell culture of a permissive host. The protein obtained with the instant invention is singularly characterized in forming empty VP2 capsids that are useful in vaccine formulation.

BACKGROUND OF THE INVENTION

The Canine Parvovirus (CPV) belongs to the autonomous parvoviruses, causing severe enteritis in dogs of all ages and myocarditis in puppies less than 12 weeks old. CPV was first isolated in 1978 (Burtonboy, G. et al., Arch. Virol. 61:1–11, 1979; Appel et al., Vet. Rec. 105. 156–179, 1979). It is believed to have arisen as a natural variant of the feline panleukopenia virus (FPLV) or the mink enteritis virus (MEV). CPV infection is controlled using conventional vaccines based on live or inactivated viruses. However, since dogs are vaccinated before pregnancy, maternal antibodies can block attenuated live vaccine replication. Autonomous parvoviruses provide a good vector for recombinant subunit vaccine production for several reasons, inter alia:
1. The capsid proteins are structurally simple (no glycosylation, phosphorylation or acetylation is required).
2. Humoral response appears to adequately control viral dissemination given the relative efficiency of inactivated vaccines.

Protein and DNA sequence studies and serologic studies show an enhanced antigenic and genetic homology between CPV, FPLV, MEV and the Raccoon Parvovirus (Tratschin et al., J. Gen Virol. 61:33–41. 1982. Carlsson et al., J. Virol., 55, 574–582, 1985. Parrish et al., Arch. Virol. 72, 267–278, 1982. Reed et al., J. Virol. 62:266–276, 1988). Despite this homology they are exquisitely specific in the "in vivo" host, although "in vitro" all viruses replicate in cat kidney cells (Appel et al., Vet. Rec. 105, 156–179, 1979. Trastschin et al., J. Gen. Virol., 61:33–41, 1982). The CPV capsid contains two proteins with broadly overlapping amino acid sequences, VP1 (82–84 KDa) and VP2 (67.70 KDa) (Paradiso et al. J. Gen. Virol. 39, 800–807, 1982. Surleraux et al. Arch Virol., 82, 233–240, 1984. J. Gen. Virol. 62, 113–125, 1982. Surleraux et al., Arch. Virol. 82, 233–240, 1984). The parvovirus capsid has a diameter of 22 nm and holds some 10 VP1 copies and some 60 VP2 copies (Wobble et al., Biochemistry 23, 6565–6569, 1984), arranged as either homo- or heterodimers (Paradiso, J. Virol., 46, 94–102, 1983) though the precise capsid structure is unknown. VP2 in full capsids (holding DNA) is preferentially broken down by proteolytic digestion into 63–67 KDa VP3 (Paradiso et al., Gen. Virol. 39, 800–807, 1982. Surleaux et al. Arch. Virol., 82, 233.240, 1984) after capsid assembly (Paradiso, J. Virol., 39, 800–807, 1981).

Our laboratory has of late been researching into the immunogenicity of various fragments of the proteins making up the CPV viral capsid which has resulted in new VP2 protein and VP2 and VP1 fragment-based recombinant vaccines being described. These findings are summarised in Spanish patent application number 9002074 for: "PRODUCTION OF CANINE PARVOVIRUS VACCINES BY VIRAL POLYPEPTIDE EXPRESSION IN *E. coli* OR BY CHEMICAL SYNTHESIS" with J. I. Casal et al. as inventors.

The said patent application relates to the expression of such products in *E. coli* bacterial vectors.

New large-scale protein production vectors have however been recently discovered based upon the replication of recombinant baculoviruses derived from the *Autographa californica* nuclear polyhedrosis virus (ACMNPV) in culture insect cells. The state of the art for these vectors is summed up in two scientific papers as follows:
1. LucKow, V. A. & Summers, M. D. (1988). Trends in the development of baculovirus expression vectors. Bio/Technology 6, 47–55.
2. J. Vialard et al. (1990). Synthesis of the membrane fusion and Hemagglutinin Proteins of Measles virus, using a novel baculovirus vector containing the β-galactosidase gene. J. Virol. 64. 37–50.

Furthermore, European Patent Application number 0 341 611 by Cornell Research Foundation, Inc. and Boyce Thompson Institute for Plant Research, Inc., describes the obtention of CPV subunit vaccines using a baculovirus expression vector other than that used in the present invention, and the said European Patent moreover fails to mention that the proteins obtained are capable of forming empty VP2 capsids thereby drawing a fundamental distinction with the instant invention inasmuch as the VP2 protein obtained under our invention is able to form empty VP2 capsids. In consequence of the above their immunogenic and hemagglutinant capacity is clearly superior as the following description will show. This added capacity of the VP2 protein obtained with our invention is further convenient in that other viral protein epitopes can be introduced in the said capsids by genetic manipulation of the recombinant baculoviruses, or by chemical manipulation of the actual capsids.

The advantages of VP2 protein synthesis in a baculovirus vector over *E. coli* synthesis are remarkable, namely a greater fidelity as to the identity of the protein obtained, a greater solubility of the product obtained, fusion proteins need not be used, etc. These are clearly advancements of and improvement to processes for obtaining recombinant subunit vaccines as regards previous processes.

SUMMARY OF THE INVENTION

The present invention puts forth a new process for producing a recombinant subunit vaccine to protect dogs from CPV, cats from FPLV and minks from MEV. The new vaccine produced thus can contain:
i) the CPV VP2 protein produced in an expression vector of baculoviruses multiplied in a cell culture of a permissive host (this protein hereinafter optionally referred to as "VP2 hereof"); or
ii) empty VP2 capsids formed by assembly of the VP2 hereof.

The VP2 protein hereof is singularly characterized in forming empty VP2 capsids, optionally incorporating other viral protein epitopes by genetic manipulation of the recombinant baculoviruses or chemical manipulation of the actual capsids.

The object of the invention is therefore a new process for obtaining new improved subunit vaccines capable of protecting dogs, cats and minks respectively from CPV, FPLV and MEV infections. As aforesaid the said vaccines can either contain the VP2 protein hereof or empty VP2 capsids formed by the said VP2 protein hereof, inasmuch as the said empty capsids have an enhanced hemagglutination activity and are highly immunogenic, excelling other recombinant proteins of these viruses produced heretofore in any other vector. The new vaccines the invention provides and being one of their objects can contain either the said empty capsids with an immunologically acceptable diluent, with or without an adjuvant, or the VP2 protein hereof together with a diluent and an adjuvant.

Since the said empty VP2 capsids can be chemically or genetically manipulated to introduce other unrelated viral protein or peptide epitopes therein, the use of the said capsids both for CPV, FPLV and MEV vaccinal purposes and modified to incorporate other epitopes, thereby to provide a polyvalent vaccine, are further additional objects of this invention.

The VP2 protein obtained with the invention and the empty VP2 capsids it can form can be useful in diagnosis to detect the presence of specific CPV antibodies or to induce polyclonal or monoclonal antibodies capable of CPV detection. The use of the VP2 protein hereof and of the chimeric capsids it can form for the above purposes is a further object of the present invention.

An additional object of this invention is a recombinant baculovirus and the process for obtaining the same, capable of producing a CPV VP2 recombinant protein identical to the viral protein, as shown in antigenic reactivity assays and other biological functionality assays. The recombinant baculovirus was called AcMNPV.pCPVEx17 and filed on 2.3.91 with the European Collection of Animal Cell Cultures, (ECACC), at Porton Down, Salisbury, Wiltshire SP4 OJG (Great Britain), accession number V91030212.

A further object of the invention is the new baculovirus transfer vector (pCPVEx17) containing the nucleic acid sequence coding for the VP2 hereof. With a process known as AcMNPV wild strain homologous recombination this new vector leads to the said AcMNPV.pCPVEx17 recombinant baculovirus.

This invention also provides the nucleic acid sequence coding for the VP2 protein of the invention (FIG. 1).

The empty CPV chimeric capsids formed by autoassembly of the CPV recombinant VP2 proteins are yet another object of this invention.

BRIEF DESCRIPTION OF THE FIGURES

SEQ. ID. NO. 1

DETAILED DESCRIPTION OF THE INVENTION

The invention provides a new process for obtaining a recombinant subunit vaccine serving to protect against infections due to Canine Parvovirus or related viruses such as FPLV and MEV. The new vaccine can contain the CPV VP2 recombinant protein produced in an expression vector of baculoviruses multiplied in a cell culture of lepidoptera or other permissive host, or empty VP2 capsids formed by aggregating the said recombinant VP2.

The invention also provides a recombinant baculovirus capable of expressing the CPV VP2 when inoculated in a permissive host, and the process for obtaining the said recombinant baculovirus.

The obtention of the recombinant baculovirus basically comprises the following steps:
a) Preparing the gene coding for the CPV VP2;
b) inserting the VP2 gene in a baculovirus transfer vector;
c) transfecting permissive host cells with the said baculovirus transfer vector holding the VP2 gene; and
d) selecting the recombinant baculovirus expressing the CPV VP2 protein.

The recombinant baculovirus obtained thus and the proteins and capsids produced are additionally characterised.

These steps will be described in detail hereinafter. The attached Sequence Listing is incorporated by reference hereto.

In a preferred embodiment the gene coding for the CPV VP2 protein is prepared in accordance with the protocol set forth in above-mentioned Spanish patent application number 9002074 and inserted in the restriction site NheI of the ACMNPV derived pJVP10Z plasmid, thereby to obtain a baculovirus transfer vector. In our invention the pCPVEx17 vector proved to have the CPV DNA adequately oriented to be expressed by the AcMNPV virus polyhedrin promoter.

The pCPVEx17 vector was used to co-transfect permissive host cells, with the AcMNPV virus wild-type strain DNA. Reference could, inter alia, be made to cells of lepidotera or their larvae. In a preferred embodiment of this invention *Spodoptera frugiperda* (*S. frugiperda*) cells, generally from the Sf9 strain, were transfected with pCPVEx17, though it can naturally be assumed that similar results would be achieved transfecting other permissive cells for recombinant baculovirus replication.

After transfection, the recombinant baculoviruses were selected after removing and titrating the floats produced in confluent monolayers of *S. frugiperda* cells. The blue plates with no trace of the viral polyhedrin under a light microscope were collected and back-titrated on *S. frugiperda* cells to obtain the recombinant baculoviruses. The AcMNPV.pCPVEx17 recombinant baculovirus is capable of expressing the CPV VP2 recombinant protein (VP2 hereof) and was filed with the ECACC, accession number V91030212. The deposit of the recombinant baculovirus has been made on Mar. 2, 1991 with the European Collection of Animal Cell Cultures (ECACC) at the PHLS Centre of Applied Microbiology and Research, Porton Down, Salisbury, Wilts. SP4 OJG, United Kingdom.

A Dot Blot assay was used to verify that the VP2 gene had been adequately integrated into the said recombinant baculovirus genome.

The proteins expressed by the *S. frugiperda* cells infected with the recombinant baculovirus were analysed by electrophoresis in SDS-polyacrylamide 8% to 15% gradient gels and were stained with Coomassie blue to observe a major presence of a protein with an estimated molecular weight of 67 KDa, equivalent to that of the viral VP2 in the recombinant virus plate. Immunodetection assays showed that the anti-CPV polyclonal antisera reacted with the VP2 expressed by the recombinant baculovirus. It was also found that neutralizing monoclonal antibodies also recognized the recombinant VP2. It can in light of these results be said that the VP2 hereof expressed by the recombinant baculovirus in S. frugiperda cells is antigenically undistinguishable from the viral VP2.

The VP2 protein obtained with the above-described process can be used for diagnosis purposes to detect the presence of specific CPV antibodies or to induce polyclonal or monoclonal antibodies capable of CPV detection. They can further be used to immunize animals to CPV and other related viruses. ELISA assays have shown that immunized animal sera recognized the viral antigens while hemagglutination inhibition assays (HI) showed that sera from animals immunized with the purified VP2 protein obtained with this invention offered HI titres equal to or greater than those obtained with other commercially available vaccines, though in some cases the response was faster and/or considerably greater when the animals were immunized with the VP2 obtained with our process (see table I).

It has also been ascertained that the VP2 protein hereof expressed by the AcMNPC.pCPVEx17 recombinant baculovirus induces antisera capable of neutralizing CPV and protecting cell monolayers up to a dilution of 1:2000 equivalent to sera from animals that are hyperimmunized or have recovered from natural infections.

Based on the results obtained, the VP2 protein expressed by the recombinant baculovirus vector hereof can be used to be formulated in vaccines in order to protect animals from infections caused by CPV and/or related viruses. These vaccines can be both passive and active. A passive vaccine could be obtained immunizing animals with the recombinant and purified VP2 hereof and then isolating polyclonal antibodies from the said VP2 which could, when purified, be used in therapeutic or prophylactic applications. An active vaccine can be prepared resuspending the VP2 hereof in an immunologically acceptable diluent with an adjuvant.

It was submitted above that the VP2 protein obtained with the process of this invention is peculiar in that it can be aggregated, working pursuant to our conditions, and form pseudo-viral empty VP2 capsids of regular and uniform structure and with a size of 22 nm, as shown by electron microscopy. No-one had to date described the "in vitro" formation of pseudo-viral capsids in Canine Parvoviruses using only the VP2 protein thereof. This much allows the recombinant VP2 proteins obtained to be easily purified. Furthermore, the empty capsids formed by VP2 assembly have an enhanced hemagglutination activity and are highly immunogenic, more so than other CPV recombinant proteins produced heretofore in other vectors. The said capsids can hence be formulated to be used in vaccines capable of protecting animals from infections caused by CPV and/or related viruses (FPLV, MEV). Broadly speaking, an active vaccine can be prepared resuspending the said capsids in an immunologically acceptable diluent, with or without an adjuvant. An important feature of these empty VP2 capsids, that could be obvious to someone skilled in the art, is that they can be chemically or genetically manipulated to introduce the protein epitopes of other viruses, infection of which is to be protected, thereby to work as a polyvalent vaccine.

Phosphate buffer saline (PBS) solutions or other like saline solutions could be used as an immunologically acceptable diluent. The adjuvant used could be alumina gel suspensions or other adjuvants regularly used in formulating vaccines.

DETAILED DESCRIPTION OF A PREFERRED EMBODIMENT OF THE INVENTION.
(EXAMPLE)

1. Obtaining Recombinant Baculoviruses Expressing the CPV VP2 Gene 1.1. Preparing the VP2 gene Isolation and cloning of the gene coding for the VP2 from the canine Parvovirus genome was described in detail in aforesaid Spanish patent application number 9002074. The said patent application describes the construction of a genomic clone containing a copy of the CPV genome from the 780916 CPV attenuated strain (Cornell University) by means of a process comprising donation of the 3' end, the central region and the 5' end into three plasmids that were then digested with the appropriate restriction enzymes to isolate the CPV genome fragments, that were isolated and ligated to each other. The structural protein VP2 gene was cloned to obtain the pCPV12 plasmid to facilitate structural gene expression.

1.2. VP2 gene insertion in a baculovirus transfer vector

A plasmidic vector AcMNPV derived with an unique cloning site NheI locus (pJVP10Z plasmid, Vialard, J. et al., J. Virol. 64, 37–50, 1990) was donated by Dr Chris Richardson (NRC. Quebec. Canada) and used to clone the XbaI fragment obtained from the pCPV12 as described in FIG. 2. The said figure shows how the pCPV12 HaII fragment containing the gene coding for the CPV VP2 was cloned in pMTL24 vector AccI site flanked by two XbaI sites, leading to the pCPV13 plasmid. The XbaI fragment of such plasmid was then inserted into the pJPV10Z NheI site. The plasmids obtained with the VP2 gene inserted were purified in accordance with the alkalyne lysis method (Brimboim & Doly. Nucleic Acids Res. 7, 1513–1523. 1979) and characterized by restriction endonuclease mapping. The pCPVEx17 recombinant proved to have adequately oriented CPV DNA for expression thereof by the AcMNPV virus polyhedrin promoter.

1.3. Recombinant virus transfection and selection

S. frugiperda cells were transfected with purified DNA mixtures from wild-type AcMNPV and pCPVEx17 plasmidic DNA in accordance with the process described by Burand et al. Virology 101. 286–290 (1980). AcMNPV DNA (1 $\mu$g) purified by the method of Smith and Summers (Virology 123, 393–406. 1983) was mixed with two different quantities of plasmidic DNA (1 and 5 $\mu$g) and taken to 750 $\mu$l with Hepes buffered saline solution (25 mM Hepes, pH 7.1, 140 mM NaCl and 125 mM $CaCl_2$). The DNA solution was inoculated onto monolayers of $2\times10^6$ S. frugiperda cells and incubated for 4 h at room temperature. The medium was then removed and 5 ml of medium containing 10% calf foetal serum added. After incubating for 4 days the supernatants were collected and titrated in confluent monolayers of S. frugiperda cells. To improve detection of the recombinant plaques the X-gal blue indicator was added to the agarose. Blue plates showing no traces of occlusion bodies (viral polyhedrin) under a light microscope were collected and back-titrated on S. frugiperda cells to obtain the recombinant viruses. After a third plating, high titre stocks of the recombinant viruses ($10^{7-8}$ pfu/ml) were obtained.

The recombinant baculovirus was called AcMNPV.pCPVEx17 and filed with the European Collection of Animal Cell Cultures (ECACC), accession number V91030212.

2. Dot Blot Assay

A Dot Blot assay was made to determine whether the VP2 gene had been integrated in the recombinant baculovirus genome, as follows.

To obtain DNA from the recombinant baculovirus the S. frugiperda cells were infected with the said virus at multiplicity of infection of 5 PFU/cell and incubated at 27° C. for 48 hours. The infected cells were collected, sonicated and centrifuged at 10000 rpm for 10 min to eliminate cell debris. The supernatants were used as starting material for the assays.

A volume of 100 µl was denatured with 10 µl of NaOH 1M, boiled for 5 min and placed immediately on ice. The mixture was neutralized with 10 µl of $PO_4H_2Na$ $1M.H_2Na$ 1M. A 20×SSC solution was added immediately to obtain a final 6×SSC concentration (SSC, citrate saline solution).

The solution was transferred to a nitrocellulose filter that had previously been moistened with 6×SSC. It was washed with more 6×SSC and dried at 37° C. for 30 min. The DNA was fixed to the nitrocellulose filter under an U.V. light for 2–3 min. The membranes were then hybridized with a specific probe of the VP2 region marked with Phosphorous-32 labeled probe at 37° C. overnight. It was then washed with decreasing SSC solutions and autoradiographed.

A strong sign of hybridization was observed only in the case of the cups containing floats from the cultures infected with recombinant viruses, which indicated that the VP2 gene had been integrated in the viral genome.

3. Protein and Immunodetection Analysis

S. frugiperda cells were infected with recombinant baculovirus at a multiplicity of 5 PFU/cell and incubated at 27° C. for 48 h. The cells were collected by centrifuging at 1000 rpm for 10 min, washed twice with phosphate buffered saline (PBS) solution pH 7.4 and resuspended at $1 \times 10^6$ cells/ml with lysis buffer (5% sodium dodecyl sulphate (SDS), 1% β-mercaptoethanol and 17.4% glycerol). The samples were charged in SDS-polyacrylamide 8 to 15% gradient gels for electrophoresis and stained with Coomasie blue or transferred to nitrocellulose membranes for immunodetection. The Coomasie blue tint showed the major presence of a protein with a virtual molecular weight of 67 KDa, equivalent to that of the VP2 viral protein in the recombinant virus plate.

For immunodetection the proteins were transferred to nitrocellulose membranes in accordance with previously described methods (Burnette, Anal. Biochem. 112. 195–203, 1981. Towbin et al., Proc. Natl. Acad. Sci. USA 76. 4350–4354. 1979). Protein transfer was made in a Phast-System (Pharmacy) apparatus. In general 25 mA/gel were used for 10–15 minutes. The nitrocellulose strips were blocked with 3% powdered skim milk in Tris HCl 20 mM pH 7.5, NaCl 500 mM (TBS) for 30 min at room temperature. The strips were then incubated for an hour at room temperature with the first anti-CPV antiserum (specific antisera or monoclonal antibodies), washed with TBS-0.05% TWEEN-20, a sorbitan derivative, namely, sorbitan mono-9-octadecenoate poly(oxy-1,2-ethanediyl)derivative, commercialized by Sigma Chemicals Company for 30 min at room temperature and incubated with anti-mouse rabbit serum where anti-CPV murine monoclonal antibodies was used as the first antibody at a dilution of 1:1000 for an hour at room temperature, or with anti-rabbit goat immunoglobulins marked with biotin (1:1000) where rabbit antisera was used as a first antibody. The strips were washed again and allowed to react with either protein A, marked with peroxidase, at a dilution of 1:1000 for an hour at room temperature, or streptavidin-peroxidase (1:2000) for 30 min at room temperature. After a thorough wash, the filters were developed with a TBS solution containing 0.5 mg/ml of 4-chloro-1-naphthol (Sigma), 17% (v/v) of methanol and 0.015% of hydrogen peroxide in TBS until visible bands appeared. The reaction was stopped treating the strips with distilled water.

Wherever specificities could be determined by immunoblot analysis all anti-CPV polyclonal antisera reacted with the VP2 protein expressed in baculovirus. The most significant feature is that all the neutralising monoclonal antibodies working in this assay also recognize recombinant VP2. This assay proves that the recombinant VP2 protein is antigenically undistinguishable from the viral VP2.

3.1. Recombinant protein and capsid purification

*S. frugiperda* cells were infected with AcMNPV.pCPVEx17 recombinant virus at a multiplicity of infection of 5–10 PFU/cell and incubated at 27° C. for 48–72 h. The cells were collected by centrifuging at 1000 rpm for 10 min, washed twice in a phosphate buffered saline solution pH 7.4 and resuspended at $2\times10^7$ cells/ml in a 25 mM pH 9.5 bicarbonate buffer. The resuspended cells were broken down by sonication and centrifuged at 10,000 rpm for 10 min to eliminate cell remains. The supernatant containing the recombinant VP2 protein can be purified using its autoaggregating capacity to form empty capsids. They are to this end either purified by 20% ammonium sulphate precipitation or the empty capsids are centrifuged on CsCl gradients at 45,000 rpm for 14 h. Capsids offer a buoyant density (ρ) of 1.30 $g/cm^3$ when banded in CsCl gradient. Preparation purity was determined by electrophoresis in SDS-polyacrylamide gels as per the method described above and VP2 protein purity turned out to be in excess of 99%.

4. Hemagglutination Activity

Recombinant protein functionality was analysed by a hemagglutination assay (HA). This activity is only associated to the particulate character of the product, thereby clearly distinguishing the same from previous ones. To this end 50 μl are mixed in a solution containing several factor two dilutions of a viral preparation with 50 μl of a solution containing 1% pig erythrocytes in phosphate buffer pH 6.5 and left at 4° C. for at least 4 h in round bottom plates.

The results show that the preparation of VP2 capsids has an HA titre of $10^5$ units/ml.

5. Confirming the Presence of Capsids by Electron Microscopy

A purified VP2 preparation was stained by negative contrast with 2% uranyl acetate and observed under an electron microscope at a magnifying power of 40,000×2.5, the presence of a large number of pseudo-viral chimeric particles of regular and uniform structure and with a size of roughly 22 nm being observed. (FIG. 3).

6. Immunizing Animals

Two New Zealand rabbits weighing 2 kg were intramuscularly immunized three times (days 0, 15 and 30) with 100 μg of a purified VP2 preparation. The first time in complete Freund adjuvant, the second and third times with Freund's incomplete adjuvant. A week after the last immunization the rabbit was bled and the serum obtained tested with an ELISA assay, an hemagglutination inhibition assay (IHA) and an in vitro CPV neutralization assay, as described hereinbelow.

On the other hand, 22 Beagle dogs, aged 45 days, grouped into four batches, were subcutaneously immunized with two doses of semi-purified VP2 capsid preparations (with β-galactosidase). Protein concentration was calculated by the Bradford assay. The second dose was provided 28 days after the first immunization. The antigen was adjuvanted with ALHYDROGEL, an aluminum hydroxide gel, commercialized by superflos (Denmark) QUIL-A, otherwise known as "Quillaic acid", a saponin adjuvant, commercialized by Superflos (Denmark), both products of Superfos of Denmark, (50 μg/dog) or a combination of both. The dogs were bled twice a week until two months after the last injection. Two dogs were immunized with an inactivated commercial vaccine. A sentinel dog was used as a negative control to check for accidental CPV exposure.

The results are set out in table I. Dogs in group I were given 100 μg of VP2 capsids per inoculation. Groups II, III and IV were respectively given 50, 25 and 10 μg per immunization.

The presence of antibodies in the dog sera was determined by an ELISA assay and by their capacity to inhibit viral HA, according to a process described hereinafter. All dogs immunized with our antigen displayed anti-CPV antibodies at various levels at the different adjuvant combinations considered (Table I). The highest antibody titres were nevertheless obtained when Quil A™ was used, alone or combined with ALHYDROGEL, an aluminum hydroxide gel. This combination was most effective at low doses (10 μg) of VP2 capsids.

HI and neutralization assays were used to assess the capacity of these preparations to induce CPV protection in dogs. Pollock and Carmichael (Cornell Vet. 72, 16–35, 1982) had previously shown that there is a good correlation between HI titre and protection; dogs showing HI>80 titres are considered refractory to CPV infection. All dogs vaccinated with our preparation showed high HI titres, between 150 and 5,120 (Table I). Sufficient HI titres lasted for over 2 months. A good correlation was found between HI titres and monolayer protection neutralisation. The titres obtained are in both cases far higher, even at lower doses (10 μg/dog) than what is needed to obtain a protective response in dogs. The titres were similar to those achieved with sera of dogs who had recovered from parvovirosis infection and much higher than those obtained with the vaccinated control. No anti-CPV antibodies were detected in the serum of dogs that were not inoculated.

A) ELISA

The presence of specific CPV antibodies in the serum of immunized animals was determined by means of an indirect ELISA assay. The antigen used was both purified virus and purified VP2 protein. Briefly, polystyrene plates were coated with 0.5 μg of virus or 0.25 μg/well of VP2 in 100 μl of carbonate buffer (0.05M, pH 9.6) at 4° C. overnight. The plates were washed with PBS (0.15M NaCl in 0.1M sodium phosphate, pH 7.4) containing 0.05% TWEEN-20™ and incubated with the antiserum for 2 h at 37° C., washed again and incubated with either anti-rabbit goat IgG marked with biotin, where rabbit sera was used, or with protein A labeled with peroxidase if dog sera were used, for 1 h at room temperature. The antibody marked with biotin was later incubated with streptavidin marked with peroxidase for 30 min at room temperature. The plates were washed again and the reaction developed with o-phenylenediamine as a substrate for the peroxidase, for 10 min in darkness, and read at 450 nm in a multichannel spectrophotometer. The results obtained were as follows:

For the rabbit sera, the ELISA titre obtained was 1/6400 for the complete virus.

For the dog sera, the antisera recognised the viral antigen in an ELISA assay perfectly, with complete virus titres of up to 1/5120 for the 100 μg dose.

B) Hemagglutination Inhibition (HI)

The sera were inactivated at 56° C. for 30 min and adsorbed with 0.25% Kaolin for 1 h at room temperature whereupon the immunized dog sera was diluted (factor two) in a phosphate buffer pH 6.5, starting with a 1:20 dilution. 25 μl of each of the previous dilutions were mixed with 25 μl of a virus dilution containing 4 units of HA, and incubated for 2 h at 37° C. 50 μl of 1% pig erythrocytes were then added in a phosphate buffer pH 6.5 and left at 4° C. for at least 4 h in round bottom plates.

C) "In vitro" CPV Neutralization

Neutralization was determined by means of a monolayer protection test. Briefly, a known quantity of CPV (100 units of HA) was incubated with rabbit antiserum at different dilutions for 2 hours at 37° C. The samples were then inoculated on CRFK susceptible cell monolayers for 90 min at 37° C. The monolayers were covered with 1 ml of agarose at 1% in a fresh medium. Five days after infection the cells were fixed with 10% formaldehyde in PBS for 20 min, the agarose was removed and the remaining cells stained with 1% violet crystal in 50% ethanol for 20 min. The level of protection was assessed by screening the infected monolayers.

The rabbit antiserum induced by the pCPVEx17 plasmid protein is able to protect the cellular monolayer from the infection up to a dilution of 1:2000, equivalent to sera from animals that are hyperimmunized or have recovered from natural infections.

TABLE I

HI TITRE IN DOGS INOCULATED WITH RECOMBINANT VP2 PARTICLES

| | | | I (100 μg) | | II (50 μg) | | | III (25 μg) | | | IV (10 μg) | | |
|---|---|---|---|---|---|---|---|---|---|---|---|---|---|
| Days | NCb | VACc | QuilA + Alum | Alum | QuilA | QuilA + Alum | Alum | QuilA | QuilA + Alum | Alum | QuilA | QuilA + Alum | Alum |
| 0 | ≦20 | ≦20 | ≦20 | ≦20 | ≦20 | ≦20 | ≦20 | ≦20 | ≦20 | ≦20 | ≦20 | ≦20 | ≦20 |
| 7 | ≦20 | ≦20 | ≦20 | ≦20 | ≦20 | ≦20 | ≦20 | ≦20 | ≦20 | ≦20 | ≦20 | ≦20 | ≦20 |
| 10 | ≦20 | ≦20 | 50 | 120 | ≦20 | 25 | 25 | 50 | 50 | ≦20 | ≦20 | 25 | ≦20 |
| 18 | ≦20 | 40 | 160 | 240 | ≦20 | ≦20 | ≦20 | 25 | 25 | ≦20 | ≦20 | ≦20 | ≦20 |
| 35 | ≦20 | 320 | 3000 | 1500 | 1200 | 1200 | 300 | 600 | 3000 | 120 | 800 | 3000 | 80 |
| 40 | ≦20 | 640 | 2000 | 2000 | 600 | 2400 | 600 | 1200 | 1200 | 300 | 600 | 2000 | 150 |
| 49 | ≦20 | 200 | 1600 | ND[d] | 600 | 800 | 75 | 500 | 500 | 100 | 300 | 900 | 50 |
| 56 | ≦20 | 50 | 400 | ND | 300 | 300 | 25 | 250 | 125 | 25 | 100 | 250 | 25 |
| 62 | ≦20 | 50 | 400 | ND | 200 | 200 | ≦20 | 125 | 125 | 25 | 250 | 75 | ≦20 | a) All the dogs were inoculated on days 0 and 28 with the said dose and adjuvant. Each value represents the average value for two dogs inoculated in the same conditions
b) Negative control
c) Dog vaccinated with a commercial inactivated vaccine
d) Not done 7. Protecting Dogs Immunized with VP2 Capsids from Virulent CPV Virus Infection In order to determine the capacity of the VP2 recombinant particles to induce protection in dogs, six dogs were infected 6 weeks after the second injection with 1 ml of virulent CPV infected dog faeces, diluted twice in PBS buffer, by oro-nasal inoculation. The clinical signs of the disease were monitored for 17 days post-infection. Rectal temperatures were recorded from day 3 post-infection. Blood samples were taken at intervals and checked for the presence of viral antibodies and for HA viremia and infection of susceptible cell cultures (Table II). The virus recovered from the dog faeces was identified as CPV by hemagglutination. All dogs immunized with the viral antigen were immune to viral infection. None of them developed any visible clinical symptom of disease or viremia. The sentinel and the vaccinated dog however offered an enhanced humoral response which indicated viral replication.

Given the significant genetic and immunologic relationship between CPV, the feline panleukopenia virus (cats) and the mink enteritis virus (minks) it could reasonably be said that the same VP2 particles may be used to render cats and minks immune to parvovirus, as is the case with conventional vaccines.

TABLE II

HI TITRE FOR DOGS STIMULATED WITH VIRULENT CPV
Days post-challenge

| DOGS | 0 | 7 | 10 | 17 |
|------|---|---|----|----|
| 1 | — | 400 | 3200 | 1600 |
| 2 | — | 1600 | 3200 | 1600 |
| 3 | 400 | 400 | 400 | 400 |
| 4 | 400 | 400 | 400 | 400 |
| 5 | 400 | 200 | 200 | 200 |
| 6 | 400 | 200 | 200 | 200 |

The dogs used in the challenge test were immunized as follows: 1. Sentinel dog. 2. Dog vaccinated with an inactivated commercial vaccine. 3. Dog vaccinated with 50 µg of VP2 adjuvanted with Quil-A (quillaic acid). 4. Dog vaccinated with 50 µg of VP2 adjuvanted with alumina and Quil-A(quillaic acid). 5. Dog vaccinated with 25 µg of VP2 adjuvanted with alumina and Quil-A(quillaic acid). 6. Dog vaccinated with 10 µg of VP2 adjuvanted with alumina and Quil-A(quillaic acid).

8. Vaccine Formulation

A passive vaccine can be obtained immunizing animals with the purified recombinant VP2 vaccines as described herein. Polyclonal antibodies directed against this VP2 can be isolated from serum, milk or other animal bodily fluids. These antibodies can then be purified and used for therapeutic or prophylactic applications.

An active vaccine can be prepared resuspending the recombinant VP2 capsids described herein in an immunologically acceptable diluent such as PBS and an adjuvant such as ALHYDROGEL™ or QuillA™. Initial and second injections or oral administration of the vaccinal solution can be used to confer immunity.

An active vaccine can also be prepared resuspending the empty capsids in an immunologically acceptable diluent with or without an adjuvant. Anyone skilled in the art will clearly see that these VP2 capsids formed only by VP2 can be chemically or genetically manipulated to introduce other viral protein epitopes and hence function as a polyvalent vaccine.

9. Conclusions

The AcMNPV.pCPVEx17 baculovirus is capable of producing a recombinant VP2 absolutely identical to the viral VP2 protein, as shown with the DNA sequence, molecular weight estimate and antigenic characterization. The VP2 obtained herein with our process is also remarkably capable of forming empty capsids, thereby providing the same with a hemagglutination and immunogenic activity that is clearly greater than in other previously described recombinant proteins, as shown with the animal immunisation tests herein described.

This enhanced immunogenic capacity can be used by those skilled in the art to present other viral protein epitopes, that can be introduced therein by either chemical or genetic manipulation of the recombinant baculoviruses.

Translation of the keys to the figures

Figure 1A:
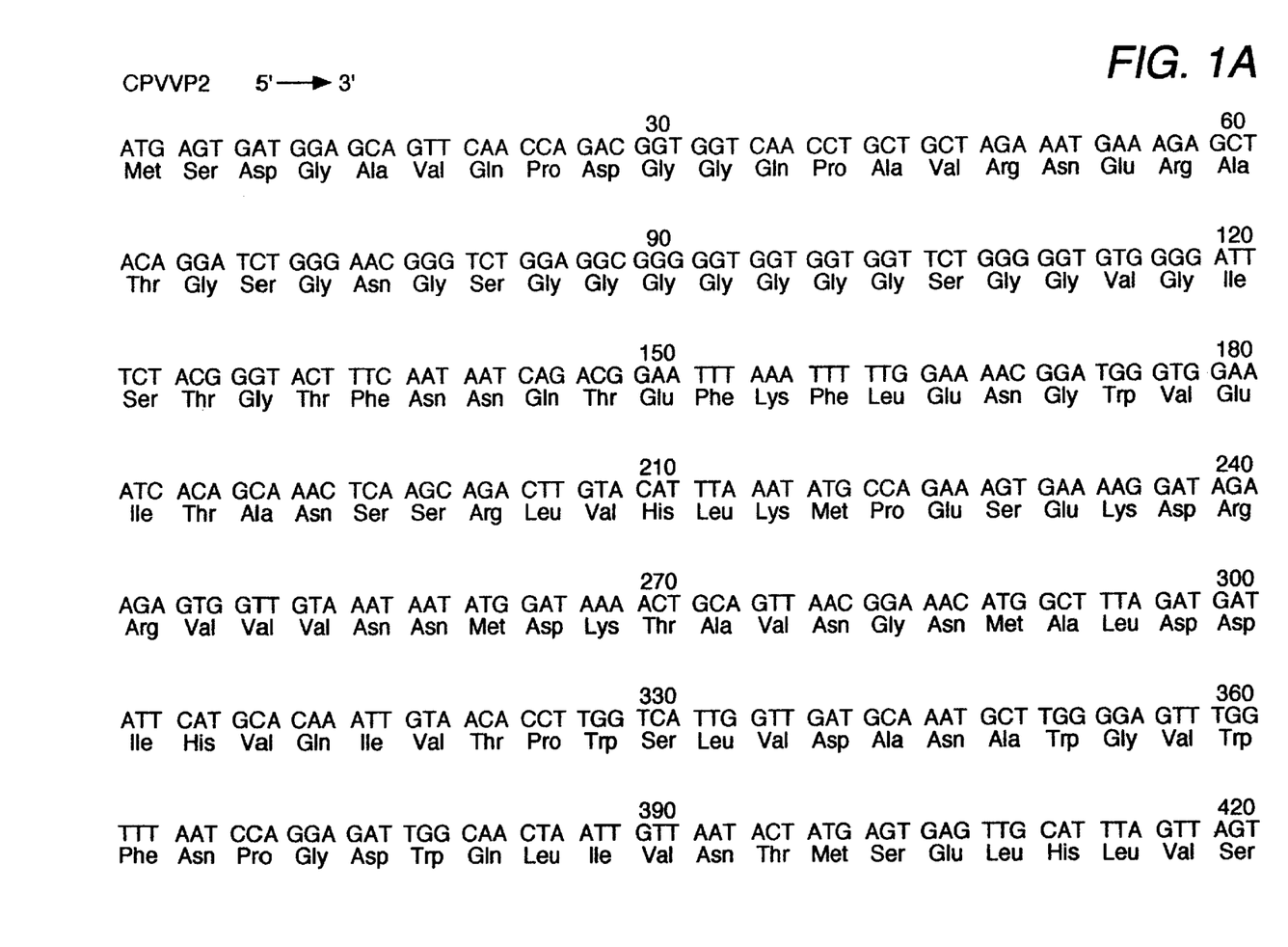
FIGS. 1A–E shows the nucleotide sequence coding for the VP2 hereof and the amino acid sequence thereof. The nucleotide sequence is shown in direction 5'→3' from left to right. The amino acids have been designated using the generally accepted three-letter code.
Figure 1B:
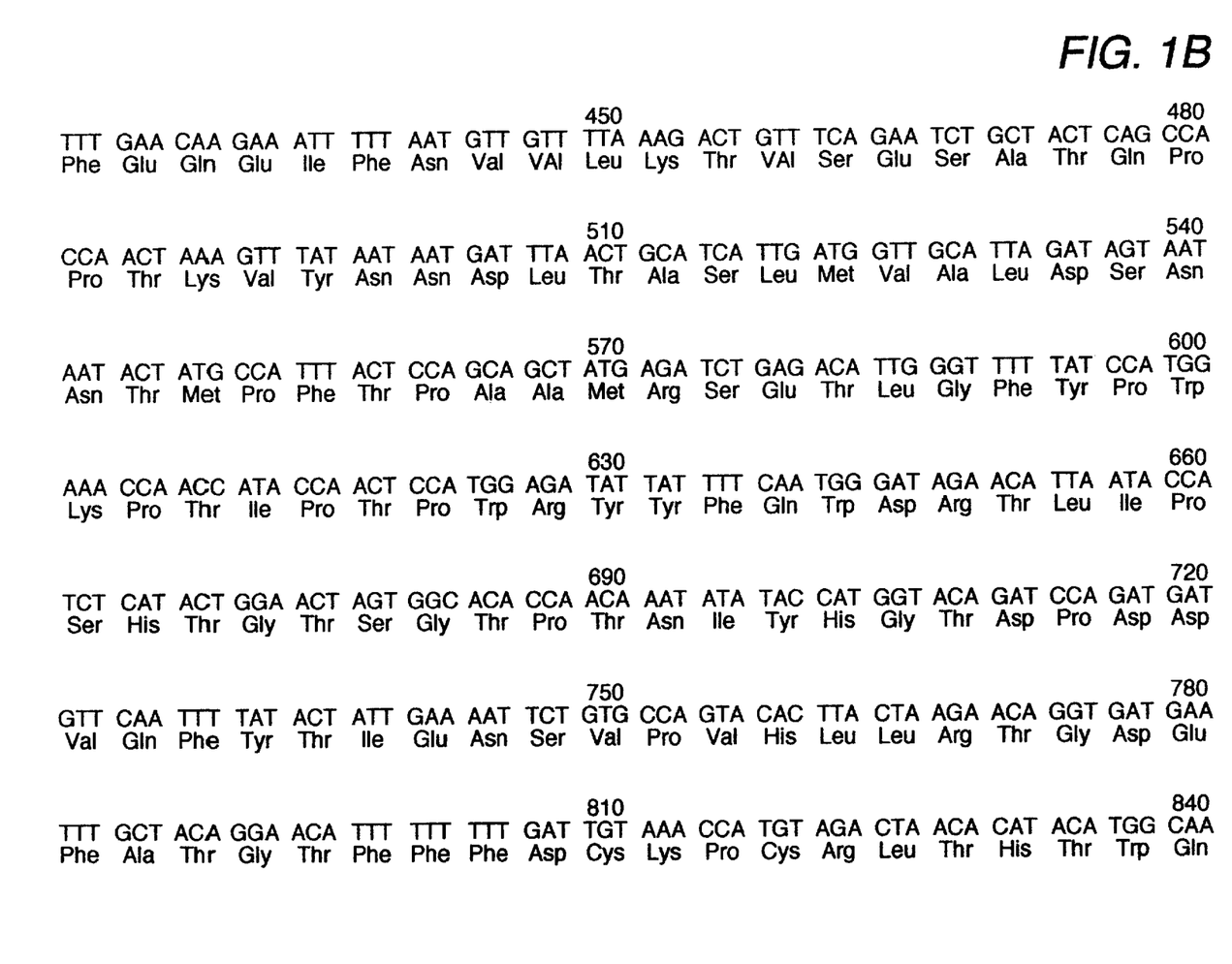
Figure 1C:
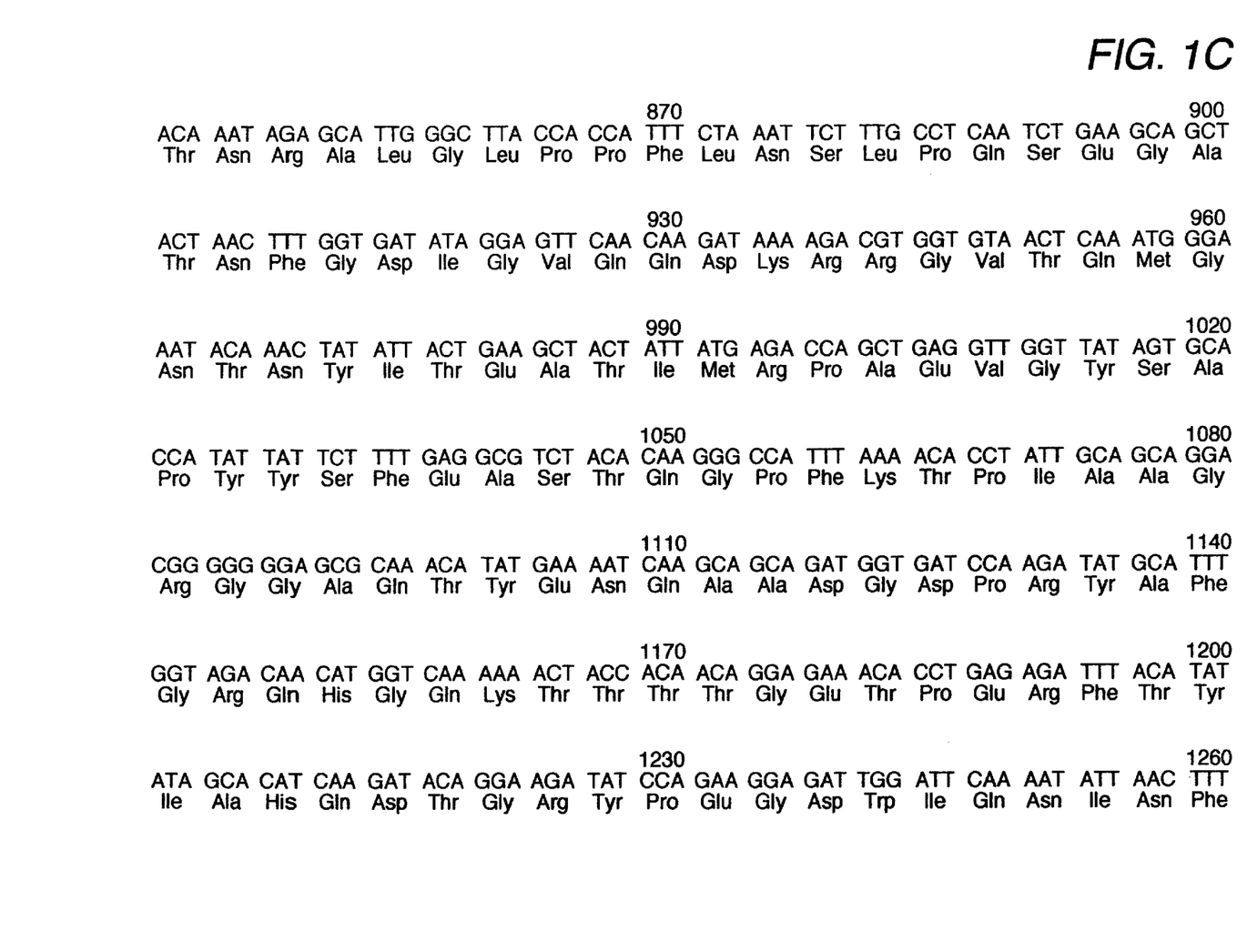
Figure 1D:
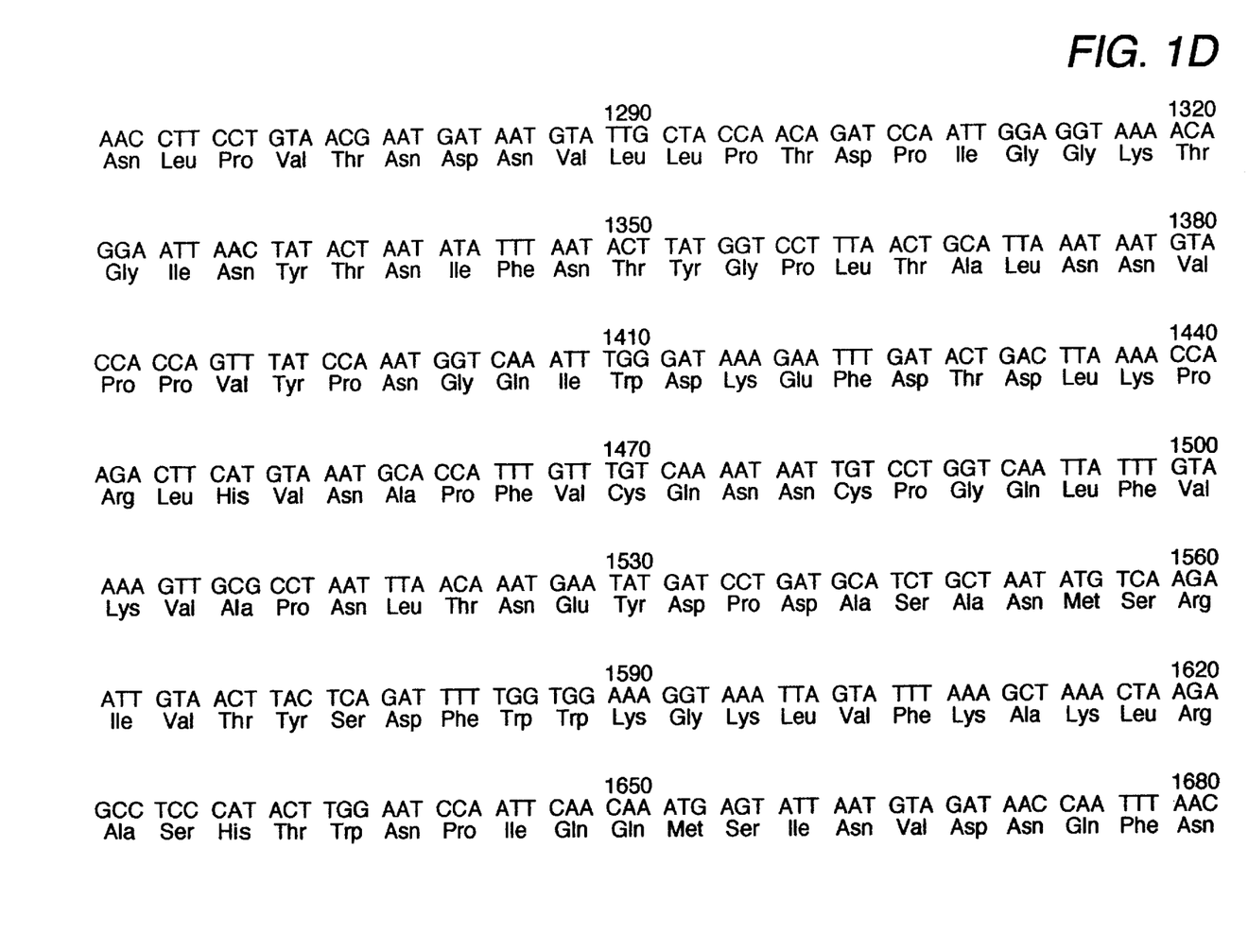
Figure 1E:
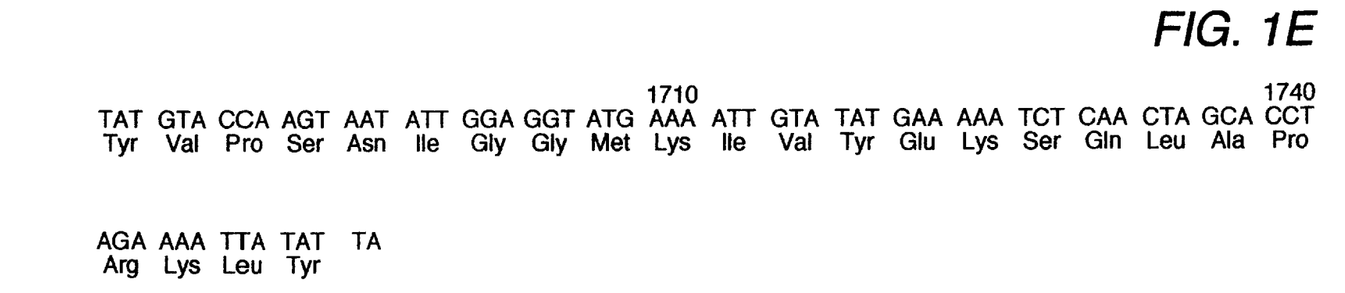
Figure 2:
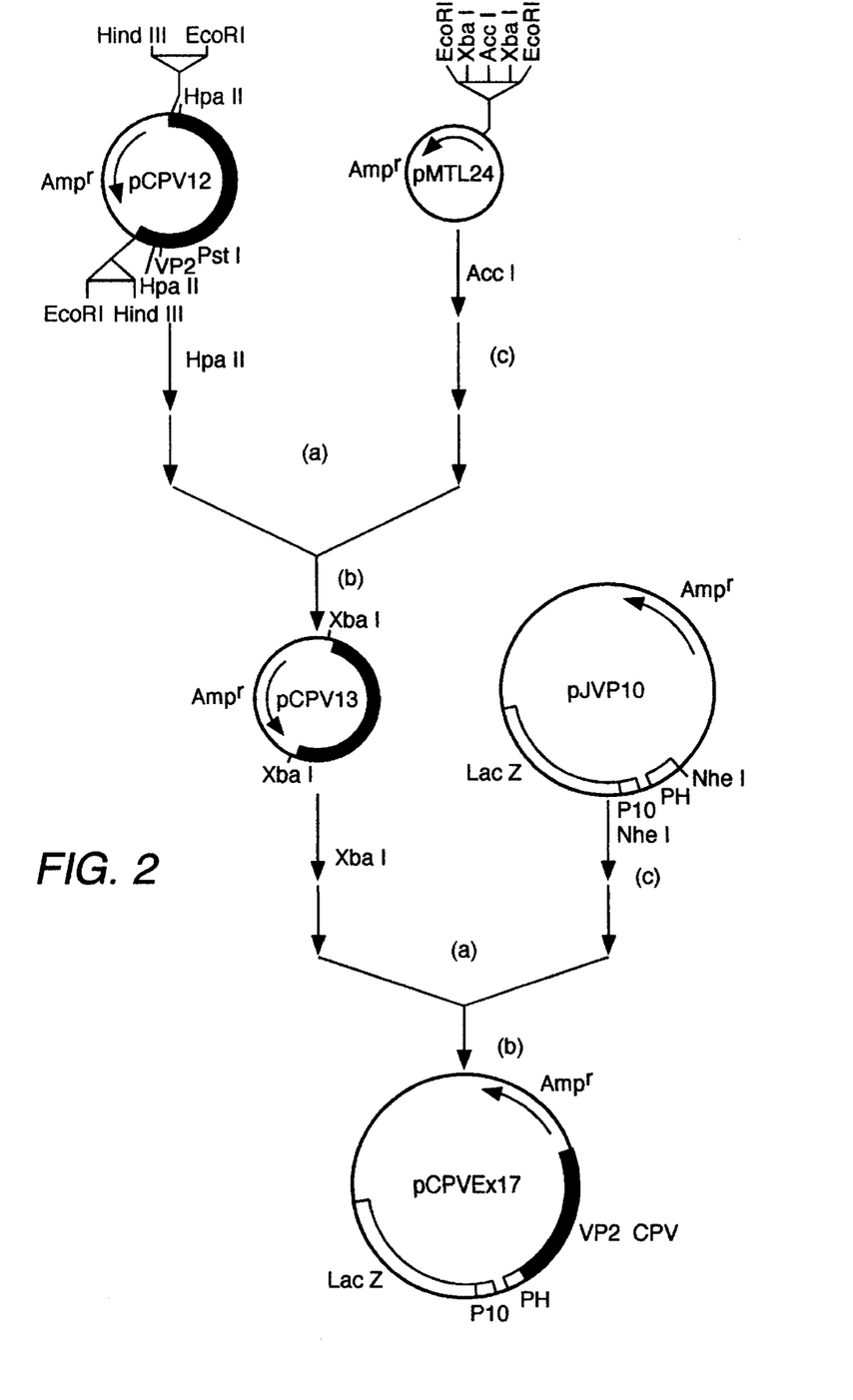
FIG. 2 shows the construction of the pCPVEx17 transfer vector, pointing out the appropriate manipulations for inserting the CPV VP2 gene in the pJVP10Z plasmid.
Figure 3:
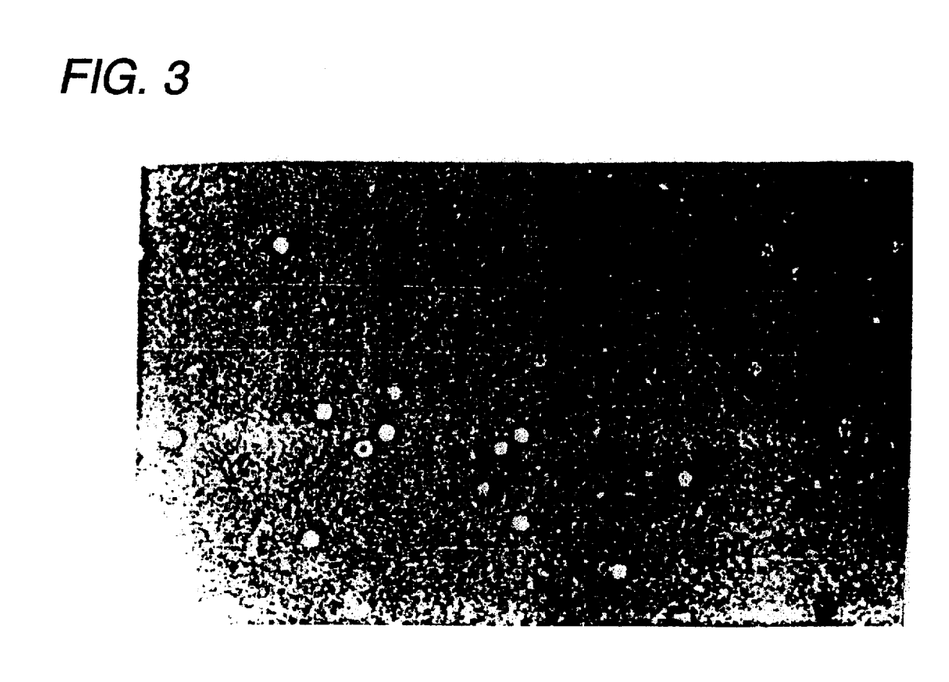
FIG. 3 shows the presence of empty VP2 capsids formed by aggregation of the VP2 protein hereof, as observed under an electron microscope.

FIG. 2

(a) Isolate agarose gel fragments.

(b) Ligate.

(c) Phosphatase.

Having described the object of the present invention what is deemed as the essence thereof is now contained in the following

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 1755 base pairs (585 amino acids)
( B ) TYPE: nucleic acid
( C ) STRANDEDNESS: single
( D ) TOPOLOGY: linear ( i i ) MOLECULE TYPE: genomic DNA ( i i i ) HYPOTHETICAL: Yes ( i v ) ANTI-SENSE: No ( v ) FRAGMENT TYPE: Complete VP2 sequence of CPV ( v i ) ORIGINAL SOURCE:
    ( A ) ORGANISM: Canine Parvovirus
    ( B ) STRAIN: CPV-N ( v i i ) IMMEDIATE SOURCE:
    ( A ) LIBRARY: Genomic ( x ) PUBLICATION INFORMATION:
    ( A ) AUTHORS:
        Reed, A.P.
        Jones, E.V.
        Miller, T.J.
    ( B ) TITLE:"NUCLEOTIDE SEQUENCE AND GENOME ORGANIZATION OF CANINE PARVOVIRUS"
    ( C ) JOURNAL: Journal of Virology
    ( D ) VOLUME: 62
    ( E ) ISSUE: 1
    ( F ) PAGES: 266-276
    ( G ) DATE: JAN, 1988
    ( K ) RELEVANT RESIDUES IN SEQ ID NO: From 1 to 1755

( x i ) SEQUENCE DESCRIPTION: SEQ ID. NO: 1:

```
ATG AGT GAT GGA GCA GTT CAA CCA GAC GGT GGT CAA CCT GCT GTC AGA                          48
Met Ser Asp Gly Ala Val Gln Pro Asp Gly Gly Gln Pro Ala Val Arg
 1           5                   10                  15

AAT GAA AGA GCT ACA GGA TCT GGG AAC GGG TCT GGA GGC GGG GGT GGT                          96
Asn Glu Arg Ala Thr Gly Ser Gly Asn Gly Ser Gly Gly Gly Gly Gly
             20                  25                  30

GGT GGT TCT GGG GGT GTG GGG ATT TCT ACG GGT ACT TTC AAT AAT CAG                         144
Gly Gly Ser Gly Gly Val Gly Ile Ser Thr Gly Thr Phe Asn Asn Gln
         35                  40                  45

ACG GAA TTT AAA TTT TTG GAA AAC GGA TGG GTG GAA ATC ACA GCA AAC                         192
Thr Glu Phe Lys Phe Leu Glu Asn Gly Trp Val Glu Ile Thr Ala Asn
     50                  55                  60

TCA AGC AGA CTT GTA CAT TTA AAT ATG CCA GAA AGT GAA AAG GAT AGA                         240
Ser Ser Arg Leu Val His Leu Asn Met Pro Glu Ser Glu Lys Asp Arg
65                  70                  75                  80

AGA GTG GTT GTA AAT AAT ATG GAT AAA ACT GCA GTT AAC GGA AAC ATG                         288
Arg Val Val Val Asn Asn Met Asp Lys Thr Ala Val Asn Gly Asn Met
                 85                  90                  95

GCT TTA GAT GAT ATT CAT GCA CAA ATT GTA ACA CCT TGG TCA TTG GTT                         336
Ala Leu Asp Asp Ile His Ala Gln Ile Val Thr Pro Trp Ser Leu Val
             100                 105                 110

GAT GCA AAT GCT TGG GGA GTT TGG TTT AAT CCA GGA GAT TGG CAA CTA                         384
Asp Ala Asn Ala Trp Gly Val Trp Phe Asn Pro Gly Asp Trp Gln Leu
         115                 120                 125

ATT GTT AAT ACT ATG AGT GAG TTG CAT TTA GTT AGT TTT GAA CAA GAA                         432
Ile Val Asn Thr Met Ser Glu Leu His Leu Val Ser Phe Glu Gln Glu
     130                 135                 140

ATT TTT AAT GTT GTT TTA AAG ACT GTT TCA GAA TCT GCT ACT CAG CCA                         480
Ile Phe Asn Val Val Leu Lys Thr Val Ser Glu Ser Ala Thr Gln Pro
145                 150                 155                 160

CCA ACT AAA GTT TAT AAT AAT GAT TTA ACT GCA TCA TTG ATG GTT GCA                         528
Pro Thr Lys Val Tyr Asn Asn Asp Leu Thr Ala Ser Leu Met Val Ala
                 165                 170                 175

TTA GAT AGT AAT AAT ACT ATG CCA TTT ACT CCA GCA GCT ATG AGA TCT                         576
Leu Asp Ser Asn Asn Thr Met Pro Phe Thr Pro Ala Ala Met Arg Ser
             180                 185                 190

GAG ACA TTG GGT TTT TAT CCA TGG AAA CCA ACC ATA CCA ACT CCA TGG                         624
Glu Thr Leu Gly Phe Tyr Pro Trp Lys Pro Thr Ile Pro Thr Pro Trp
         195                 200                 205

AGA TAT TAT TTT CAA TGG GAT AGA ACA TTA ATA CCA TCT CAT ACT GGA                         672
Arg Tyr Tyr Phe Gln Trp Asp Arg Thr Leu Ile Pro Ser His Thr Gly
     210                 215                 220

ACT AGT GGC ACA CCA ACA AAT ATA TAC CAT GGT ACA GAT CCA GAT GAT                         720
```

```
Thr  Ser  Gly  Thr  Pro  Thr  Asn  Ile  Tyr  His  Gly  Thr  Asp  Pro  Asp  Asp
225            230                      235                      240

GTT  CAA  TTT  TAT  ACT  ATT  GAA  AAT  TCT  GTG  CCA  GTA  CAC  TTA  CTA  AGA        768
Val  Gln  Phe  Tyr  Thr  Ile  Glu  Asn  Ser  Val  Pro  Val  His  Leu  Leu  Arg
               245                      250                      255

ACA  GGT  GAT  GAA  TTT  GCT  ACA  GGA  ACA  TTT  TTT  TTT  GAT  TGT  AAA  CCA        816
Thr  Gly  Asp  Glu  Phe  Ala  Thr  Gly  Thr  Phe  Phe  Phe  Asp  Cys  Lys  Pro
                    260                      265                      270

TGT  AGA  CTA  ACA  CAT  ACA  TGG  CAA  ACA  AAT  AGA  GCA  TTG  GGC  TTA  CCA        864
Cys  Arg  Leu  Thr  His  Thr  Trp  Gln  Thr  Asn  Arg  Ala  Leu  Gly  Leu  Pro
               275                      280                      285

CCA  TTT  CTA  AAT  TCT  TTG  CCT  CAA  TCT  GAA  GGA  GCT  ACT  AAC  TTT  GGT        912
Pro  Phe  Leu  Asn  Ser  Leu  Pro  Gln  Ser  Glu  Gly  Ala  Thr  Asn  Phe  Gly
          290                      295                      300

GAT  ATA  GGA  GTT  CAA  CAA  GAT  AAA  AGA  CGT  GGT  GTA  ACT  CAA  ATG  GGA        960
Asp  Ile  Gly  Val  Gln  Gln  Asp  Lys  Arg  Arg  Gly  Val  Thr  Gln  Met  Gly
305                      310                      315                      320

AAT  ACA  AAC  TAT  ATT  ACT  GAA  GCT  ACT  ATT  ATG  AGA  CCA  GCT  GAG  GTT       1008
Asn  Thr  Asn  Tyr  Ile  Thr  Glu  Ala  Thr  Ile  Met  Arg  Pro  Ala  Glu  Val
                    325                      330                      335

GGT  TAT  AGT  GCA  CCA  TAT  TAT  TCT  TTT  GAG  GCG  TCT  ACA  CAA  GGG  CCA       1056
Gly  Tyr  Ser  Ala  Pro  Tyr  Tyr  Ser  Phe  Glu  Ala  Ser  Thr  Gln  Gly  Pro
               340                      345                      350

TTT  AAA  ACA  CCT  ATT  GCA  GCA  GGA  CGG  GGG  GGA  GCG  CAA  ACA  TAT  GAA       1104
Phe  Lys  Thr  Pro  Ile  Ala  Ala  Gly  Arg  Gly  Gly  Ala  Gln  Thr  Tyr  Glu
          355                      360                      365

AAT  CAA  GCA  GCA  GAT  GGT  GAT  CCA  AGA  TAT  GCA  TTT  GGT  AGA  CAA  CAT       1152
Asn  Gln  Ala  Ala  Asp  Gly  Asp  Pro  Arg  Tyr  Ala  Phe  Gly  Arg  Gln  His
     370                      375                      380

GGT  CAA  AAA  ACT  ACC  ACA  ACA  GGA  GAA  ACA  CCT  GAG  AGA  TTT  ACA  TAT       1200
Gly  Gln  Lys  Thr  Thr  Thr  Thr  Gly  Glu  Thr  Pro  Glu  Arg  Phe  Thr  Tyr
385                      390                      395                      400

ATA  GCA  CAT  CAA  GAT  ACA  GGA  AGA  TAT  CCA  GAA  GGA  GAT  TGG  ATT  CAA       1248
Ile  Ala  His  Gln  Asp  Thr  Gly  Arg  Tyr  Pro  Glu  Gly  Asp  Trp  Ile  Gln
                    405                      410                      415

AAT  ATT  AAC  TTT  AAC  CTT  CCT  GTA  ACG  AAT  GAT  AAT  GTA  TTG  CTA  CCA       1296
Asn  Ile  Asn  Phe  Asn  Leu  Pro  Val  Thr  Asn  Asp  Asn  Val  Leu  Leu  Pro
               420                      425                      430

ACA  GAT  CCA  ATT  GGA  GGT  AAA  ACA  GGA  ATT  AAC  TAT  ACT  AAT  ATA  TTT       1344
Thr  Asp  Pro  Ile  Gly  Gly  Lys  Thr  Gly  Ile  Asn  Tyr  Thr  Asn  Ile  Phe
          435                      440                      445

AAT  ACT  TAT  GGT  CCT  TTA  ACT  GCA  TTA  AAT  AAT  GTA  CCA  CCA  GTT  TAT       1392
Asn  Thr  Tyr  Gly  Pro  Leu  Thr  Ala  Leu  Asn  Asn  Val  Pro  Pro  Val  Tyr
     450                      455                      460

CCA  AAT  GGT  CAA  ATT  TGG  GAT  AAA  GAA  TTT  GAT  ACT  GAC  TTA  AAA  CCA       1440
Pro  Asn  Gly  Gln  Ile  Trp  Asp  Lys  Glu  Phe  Asp  Thr  Asp  Leu  Lys  Pro
465                      470                      475                      480

AGA  CTT  CAT  GTA  AAT  GCA  CCA  TTT  GTT  TGT  CAA  AAT  AAT  TGT  CCT  GGT       1488
Arg  Leu  His  Val  Asn  Ala  Pro  Phe  Val  Cys  Gln  Asn  Asn  Cys  Pro  Gly
                    485                      490                      495

CAA  TTA  TTT  GTA  AAA  GTT  GCG  CCT  AAT  TTA  ACA  AAT  GAA  TAT  GAT  CCT       1536
Gln  Leu  Phe  Val  Lys  Val  Ala  Pro  Asn  Leu  Thr  Asn  Glu  Tyr  Asp  Pro
               500                      505                      510

GAT  GCA  TCT  GCT  AAT  ATG  TCA  AGA  ATT  GTA  ACT  TAC  TCA  GAT  TTT  TGG       1584
Asp  Ala  Ser  Ala  Asn  Met  Ser  Arg  Ile  Val  Thr  Tyr  Ser  Asp  Phe  Trp
          515                      520                      525

TGG  AAA  GGT  AAA  TTA  GTA  TTT  AAA  GCT  AAA  CTA  AGA  GCC  TCC  CAT  ACT       1632
Trp  Lys  Gly  Lys  Leu  Val  Phe  Lys  Ala  Lys  Leu  Arg  Ala  Ser  His  Thr
     530                      535                      540

TGG  AAT  CCA  ATT  CAA  CAA  ATG  AGT  ATT  AAT  GTA  GAT  AAC  CAA  TTT  AAC       1680
```

| | | | | | | | | | | | | | | |
|---|---|---|---|---|---|---|---|---|---|---|---|---|---|---|
| Trp | Asn | Pro | Ile | Gln | Gln | Met | Ser | Ile | Asn | Val | Asp | Asn | Gln | Phe | Asn |
| 545 | | | | | 550 | | | | | 555 | | | | | 560 |

| | | | | | | | | | | | | | | |
|---|---|---|---|---|---|---|---|---|---|---|---|---|---|---|
| TAT | GTA | CCA | AGT | AAT | ATT | GGA | GGT | ATG | AAA | ATT | GTA | TAT | GAA | AAA | TCT | 1728 |
| Tyr | Val | Pro | Ser | Asn | Ile | Gly | Gly | Met | Lys | Ile | Val | Tyr | Glu | Lys | Ser | |
| | | | | 565 | | | | | 570 | | | | | 575 | | |

| | | | | | | | |
|---|---|---|---|---|---|---|---|
| CAA | CTA | GCA | CCT | AGA | AAA | TTA | TAT | TAA | 1755 |
| Gln | Leu | Ala | Pro | Arg | Lys | Leu | Tyr | End | |
| | | | 580 | | | | | 585 | |

We claim:

1. A recombinant subunit vaccine for protecting dogs from canine parvovirus (CPV) infection comprising:
   an immunizing quantity of isolated empty CPV capsids each consisting of autoassembled CPV recombinant VP2 protein; and
   a diluent and an adjuvant.

2. A method for protecting dogs from infection caused by canine parvovirus (CPV) comprising the step of:
   administering to a dog a protective dosage of a vaccine of isolated empty CPV capsids each consisting of an autoassembled recombinant VP2 protein, said vaccine also containing a diluent and an adjuvant.

* * * * *